United States Patent [19]
Meybeck et al.

[11] Patent Number: 5,747,538
[45] Date of Patent: May 5, 1998

[54] USE OF GINSENOSIDE $R_0$ OR A PLANT EXTRACT CONTAINING SAME TO PROMOTE COLLAGEN SYNTHESIS

[75] Inventors: Alain Meybeck; Frédéric Bonte, both of Courbevoie; Marc Dumas, Colombes; Catherine Chaudagne, Chatou, all of France

[73] Assignee: L.V.M.H. Recherche, Nanterre, France

[21] Appl. No.: 716,363

[22] PCT Filed: Mar. 17, 1995

[86] PCT No.: PCT/FR95/00326

§ 371 Date: Sep. 18, 1996

§ 102(e) Date: Sep. 18, 1996

[87] PCT Pub. No.: WO95/25524

PCT Pub. Date: Sep. 28, 1995

[30] Foreign Application Priority Data

Mar. 18, 1994 [FR] France .................. 94 03194

[51] Int. Cl.$^6$ .................................................. A61K 7/48
[52] U.S. Cl. .............. 514/570; 424/78.03; 424/78.06; 424/40.1; 514/828; 514/887; 536/4.1
[58] Field of Search ................. 424/78.03, 78.06, 424/40.1; 514/828, 887, 570

[56] References Cited

U.S. PATENT DOCUMENTS

| | | | |
|---|---|---|---|
| 4,317,816 | 3/1982 | Arichi | 424/182 |
| 5,243,094 | 9/1993 | Borg | 568/822 |
| 5,401,502 | 3/1995 | Wunderlich | 424/195 |
| 5,564,207 | 10/1996 | Kashibuchi | 424/401 |

FOREIGN PATENT DOCUMENTS

| | | |
|---|---|---|
| 1031023 | 2/1989 | China. |
| 2309210 | 11/1976 | France. |
| 2695561 | 3/1994 | France. |
| 55-129228 | 10/1980 | Japan. |
| 61-056114 | 3/1986 | Japan. |
| 4-334308 | 11/1992 | Japan. |
| 5-262635 | 10/1993 | Japan. |

OTHER PUBLICATIONS

"Recent Advances in Ginseng Research in China", Liu Cx et al., Feb. 1992, vol. 36, No. 1, J. Ethnopharmacol, pp. 27–38.

"Dermocosmetic Activity of Ginsenosides. Note II: Instrumental Evaluation of Cutaneous Hydration and Elasticity", A. Gezzi et al., 1986, vol. 57, Fitoterapia, pp. 15–28.

"Dermocosmetic Activity of Ginsenosides. Note III: Long-Term Evaluation of the Moisturizing and Tonifying Effect on the Face Skin", S.B. Curri et al., 1986, vol. 57, Fitoterapia, pp. 217–222.

"Effect of Panax Ginseng on the Production o fGlycosaminoglycans in Cultured Human Skin Fibroblast", H. Tanaka et al., 1991, vol. 115, No. 22, Chemical Abstracts, p. 464, col. 2.

*Primary Examiner*—Thurman K. Page
*Assistant Examiner*—D. Faulkner
*Attorney, Agent, or Firm*—Lowe, Price, LeBlanc & Becker

[57] ABSTRACT

The use of ginsenoside $R_o$ or a plant extract containing same to prepare a cosmetic or pharmaceutical composition, particularly a skin care composition, for promoting collagen synthesis, particularly collagen I and/or collagen III synthesis. Said cosmetic or pharmaceutical composition is administered to a mammal, particularly a human being, in order to promote collagen synthesis. A method for promoting collagen synthesis in fibroblast growth media is also disclosed.

14 Claims, No Drawings

USE OF GINSENOSIDE $R_0$ OR A PLANT EXTRACT CONTAINING SAME TO PROMOTE COLLAGEN SYNTHESIS

This application is a 37T of PCT/FR95/00326 published Mar. 17, 1995.

The invention relates to the use of ginsenoside $R_O$ and plant extracts in which it is present for the preparation of cosmetic or pharmaceutical compositions, especially dermatological compositions, for stimulating the synthesis of collagen, particularly collagen I and collagen III. It further relates to fibroblast culture media containing ginsenoside $R_O$ or plant extracts in which it is present.

The Panax family is known by its numerous varieties, the best known of which are as follows:

*Panax ginseng* (C. A. Meyer), which is most frequently used for its medical attributes,

*Panax notoginseng,*

*Panax pseudo-ginseng* (subsp. *himalaicus*),

*Panax japonicus* (var. *major*; var. *angustifolius*),

*Panax quinquefolium,*

*Panax trifolius,*

*Panax zingiberensis* and

*Panax stipuleanatus.*

*Panax ginseng* seems to be among the most saponin-rich and the most effective.

Panax originate essentially from three countries:

Japan

China

Korea.

The varieties cultivated in these different zones can be slightly different and are exposed to different geoclimatic conditions.

Nevertheless, it is found for example that the best quality of *ginseng* comes from China and then from Japan.

A *ginseng* tuber reaches maturity in 4 to 6 years. The optimal quality is obtained with 6-year-old tubers.

Very different saponin contents are found in the different parts of the plant. The root part is the most frequently used and generally the most active.

The highest saponin content is observed in the end of the root (*ninjin* in Japanese) and in the hairy roots (*keninjin* in Japanese).

The saponins most frequently encountered in the plants of the Panax family are of the damaran type. However, among the *Panax saponins*, there is one particular saponin, ginsenoside $R_O$ or Chikusetsusaponin V, which has an oleanan structure of the following formula:

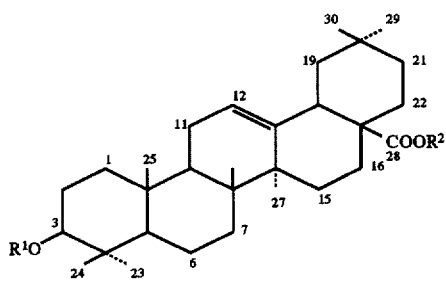

in which:

the substituent $R^1$ in the 3-position consists of two sugars linked together, namely a beta-D-glucuronopyranoside and a beta-D-glucopyranosyl, represented symbolically by GlcA $_2$Glc, and the substituent $R^2$ in the 28-position is a beta-D-glucopyranosyl, represented symbolically by Glc.

There is a high proportion of this ginsenoside in *Panax japonicus* (Japanese) and Chinese *P. japonicus*, *P. japonicus* var. *mayor* and *P. japonicus* var. *angustifolius*, as is apparent from the following literature reference:

MORITA T., KASAI R., KOHDA H., TANAKA O., ZHOU J., TSUNG-REN Yang

Chemical and Morphological study on Chinese *Panax japonicus* C. A. MEYER

Chem. Pharm. Bull., 1983, 31, 9-3205 - 2309.

In Japan, *P. japonicus* is also known under the name Chikusetsu Ninjin. The structure of Chikusetsusaponin V was described in 1971 by:

KONDO N., MARUMOTO Y., SHOJI J., Studies on the constituents of Panacis Japonici Rhizoma. IV The structure of chikusetsusaponin V. Chem. Pharm. Bull. (1971) 19 (6), 1103–1107.

This natural molecule can be extracted in particular by the process described by J. SHOJI in Advances in Chinese Medicinal Material Research 1985, p. 455 et seq.

Different uses, in particular in the medical field, of ginsenosides and particularly ginsenoside $R_O$ have been described in the literature; thus:

an antiviral activity of different ginsenosides, including ginsenosides $R_0$, is described by Li, Jingbo et al. in Baiqiien Yike Daxue Xuebao 1992, 18(1), 24–26, a protective activity of ginsenoside $R_0$ in association with ginsenoside Rb on the aortic endothelium is described by Liao, Duanfang et al. in Hunan Yike Daxue Huebao 1992, 17(1), 13–15, patent JP 04 005 235, 1992, describes the use of ginsenoside for the treatment of hepatitis, Japanese patent JP 55 122 721 describes the use of ginsenoside $R_0$ as an antidiabetic, Kuo S. C. et al., in a Planta Med. 1990, 56(2), 164–167, describe its use as a platelet aggregation inhibitor, Planta Med. 1990, 56(1), 19–23, describe its use as an anti-inflammatory.

Different documents also describe the use of *Panax japonicus* extracts in the cosmetic field. The following may be cited in this connection:

Japanese patent JP 61 047 411, which describes the use of such extracts for promoting hair growth, Japanese patent JP 62 093 217, which describes the use of a *Panax japonicus* extract as a hair tonic, Japanese patent JP 61 289 008, which relates to a cosmetic composition containing an extract of *Panax japonicus* roots in combination with mucopolysaccharides.

It has now been discovered that ginsenoside $R_0$ and plant extracts in which it is present have a surprising stimulating activity on the synthesis of collagen, particularly collagens of types I and III, hereafter abbreviated respectively to "collagen I" and "collagen III", which makes them particularly useful for combating the effects of skin ageing and for firming the skin or improving healing.

Changes in the appearance and especially the mechanical properties of the skin are in fact essentially due to changes in the components of the dermis.

Now, type I collagen represents 80 to 90% of the total skin collagen, the remainder, i.e. about 10 to 15% of the total skin collagen, consisting mainly of type III collagen. Type I and type III collagens are very intimately associated to form fibers within the dermis (BOREL J. P., MONBOISSE J. C., C. R. Soc. Biol. (1993), 187, 124–142; LAPERE C. M., Br. J. Dermatol. (1990), 122, 5–11).

Substantial decreases in the proportion of collagens I and III in human skin during ageing have been reported (DUMAS M., CHAUDAGNE C., BONTE F., MEYBECK A., Mech. Ageing Dev. (accepted for publication). VITELLARO-ZUCCARELLO L., GARBELLI R., DAL POZZO ROSSI V., Cell Tissue Res., (1992), 268, 505–511). The pertinence of these results is confirmed by the observation that the expression of the genes coding for collagens I and III decreases with age (CHEN Y. Q., MAUVIER R., TAN E. M., UITTO J., J. Invest. Dermatol., (1993), 100, 535).

The drop in the proportion of collagens I and III in the skin can also be induced by therapeutic treatments such as the topical application of gluco-corticoids (OIKARINEN A., AUTIO P., KIISTALA U., RISTELLI L., RISTELI J., J. Invest. Dermatol., (1992), 98, 220–225).

Thus, irrespective of its origin, whether it be spontaneous as in the case of natural ageing, or whether it be induced by a pathological condition, by drugs or by exposure to ultraviolet radiation, the decrease in the proportion of collagens I and III can be slowed down, or even stopped, by carrying out the present invention in order to stimulate collagen synthesis.

The main object of the present invention is therefore to solve the technical problem which consists in providing a novel formulation of a cosmetic or pharmaceutical composition, especially dermatological composition, having a good efficacy in preventing or treating the effects of skin ageing and in firming the skin or for improving healing.

Thus, according to a first feature, the present invention relates to the use of ginsenoside $R_0$ or a plant extract in which it is present for the preparation of a cosmetic or pharmaceutical composition, especially dermatological composition, for stimulating the synthesis of collagen, particularly collagen I and/or collagen III.

According to one variant, the abovementioned composition is intended for preventing or treating the effects of skin ageing, whether it be of actinic or spontaneous (chronological) origin.

According to another variant, the abovementioned composition is intended for promoting the formation of the skin tissue system.

According to yet another variant, the composition is intended for firming the skin.

According to yet another variant, the composition is intended for healing skin wounds.

If the composition comprises a plant extract containing ginsenoside $R_0$, this plant extract is preferably obtained from Japanese *Panax japonicus*, Chinese *Panax japonicus*, *Panax japonicus* var. *mayor* or *Panax japonicus* var. *angustifolius*, preferably from the roots of these plants.

According to one particularly advantageous variant of the invention, the abovementioned extract is obtained from the roots by extraction with a polar solvent, such as methanol, under reflux.

According to another variant, the plant extract can be obtained from roots by extraction with petroleum ether, followed by re-extraction with a polar solvent, such as methanol, and precipitation with acetone.

According to other variants of the invention, the plant extract may be obtained by any process which produces an extract containing at least 1% of ginsenoside $R_0$.

The cosmetic composition which can be used according to the invention is intended for stimulating the synthesis of collagen, particularly that of collagen I and/or collagen III, and contains as the active ingredient a cosmetically effective amount of ginsenoside $R_0$ or a plant extract in which it is present.

The composition is intended especially for promoting the synthesis of the skin tissue system, for firming the skin and for healing skin wounds.

It is therefore very particularly intended for combating the effects of skin ageing or for firming the skin.

Such a composition can advantageously be used for example as a composition for preventing the appearance of wrinkles or reducing the depth of wrinkles.

The pharmaceutical compositions which can be used according to the invention are intended for improving healing or for treating the diverse pathological conditions which are accompanied by a collagen deficiency.

According to another feature, the invention further relates to a method of cosmetic or therapeutic treatment, especially dermatological treatment, for a mammal, particularly a human being, said method being characterized in that a cosmetically or therapeutically effective amount of ginsenoside $R_0$ or a plant extract in which it is present is administered to said mammal in order to stimulate the synthesis of collagen, particularly collagen I and/or collagen III, and especially for promoting the synthesis of the skin tissue system or for firming the skin.

According to one advantageous embodiment of this method, the ginsenoside $R_0$ or a plant extract in which it is present is administered in an amount which is effective for improving healing or treating collagen deficiencies of diverse origins.

Other variants of the method according to the invention will become clearly apparent to those skilled in the art from the description, taken in its entirety, and from the claims.

In each of the foregoing features, the ginsenosides $R_0$ will preferably be used in concentrations of between 0.001 and 5% by weight, based on the total weight of said composition.

This concentration will preferably be between 0.001 and 1% by weight, based on the total weight of said composition.

According to one particularly valuable variant of the invention, the composition according to the invention will also contain a Centella asiatica extract, asiatic acid, madecassic acid or asiaticoside.

It may also advantageously comprise a horse chestnut extract, a knee holly extract, madecassoside, ivy saponins, sericoside, alpha-hydroxy acids, alpha-ketoglutarate, ascorbic acid, proline, L-hydroxyproline, lysine, hydroxylysine, glycine or forskolin, a derivative thereof or a plant extract in which it is present.

It may also advantageously comprise collagenase inhibitors or inhibitors of collagenase biosynthesis, for example retinoic acid.

Within the framework of the invention, the ginsenoside $R_0$ or a plant extract in which it is present is administered by the conventional methods affording the stimulation of collagen synthesis. The simplest method of administration is usually the topical method, particularly when the aim is to synthesize the skin tissue system, firm the skin and heal skin wounds.

According to one advantageous variant of the invention, the ginsenoside $R_0$ or a plant extract in which it is present is incorporated in a cosmetically or pharmaceutically acceptable, especially dermatologically acceptable, excipient, vehicle or carrier. Such carriers are well known to those skilled in the art and can also be found in the Examples of cosmetic compositions or pharmaceutical compositions, especially dermatological compositions, described below, which have a general scope.

According to another of its features, the invention relates to the use of ginsenoside $R_0$ or a plant extract in which it is present as an agent for stimulating the synthesis of collagen I and/or collagen III.

It relates very particularly to the use of ginsenoside $R_0$ or a plant extract in which it is present as a constituent of a culture medium for improving the synthesis of collagen I and/or collagen III in a fibroblast culture.

This agent can be used in any fibroblast culture medium, particularly in a medium in which the fibroblasts are included in a matrix, for example a polymer matrix.

The invention further relates to a process for stimulating the synthesis of collagen I and/or collagen III, which consists in introducing ginsenoside $R_0$ or a plant extract in which it is present into a fibroblast culture medium.

In this process, it is preferable to introduce 0.001 to 0.1% of ginsenoside $R_0$ into a medium denoted by E199-C hereafter, which is obtained by introducing L-glutamine at a concentration of 2 mmol/l into an E199 medium marketed by GIBCO.

The above-described plant extracts containing ginsenoside $R_0$ can also be used for the preparation of the above culture media.

Other objects, characteristics and advantages of the invention will become clearly apparent from the following explanatory description referring to several Examples, which are given solely by way of illustration and consequently cannot in any case limit the scope of the invention.

Unless indicated otherwise, the percentages in the Examples are expressed by weight. In the case of the extracts, their amounts are expressed by dry weight.

EXAMPLE 1

Preparation of an extract

The extraction is performed on roots of Panax japonicus C. A. Meyer.

After the roots have been ground, they are extracted with methanol under reflux for 4 h to give a brown paste. The yield is about 33% and the content of ginsenoside $R_0$ is about 25%.

EXAMPLE 2

Preparation of an extract

Roots of Panax japonicus C. A. Meyer are used.

38.56 g of the ground roots are extracted in a Soxhlet apparatus for 12 h with 140 ml of petroleum ether.

The residue is re-extracted in the Soxhlet apparatus with 130 ml of methanol for 20 h.

The 130 ml of methanol are concentrated under vacuum on a rotary evaporator to reduce the volume to 45 ml.

After cooling, the solution is filtered on Millex SR of porosity 0.45 micron.

The solution obtained is added all at once to 500 ml of anhydrous acetone. The beige precipitate obtained is filtered off, washed with anhydrous acetone and dried in an oven at 45° C.

This gives 6.13 g of a light beige powder (yield 15.9%). The content of ginsenoside $R_0$ is about 35%.

EXAMPLE 3

Demonstration of the stimulation of collagen I synthesis a) Protocol

An ELISA method is used to measure collagen I synthesis, with and without treatment, on a culture of fibroblasts originating from a face lift performed on a 50-year-old woman.

a.1) Fibroblast cultures:

The fibroblasts are cultivated by the explant method up to the point of confluence, at 37° C., in a medium consisting of a mixture of E199-C medium and 10% fetal calf serum, in a humidity-saturated atmosphere containing 5% of $CO_2$.

Then, after detachment with an isotonic solution containing 0.1% of trypsin and 0.02% of EDTA, buffered to pH 7.2, the cells are inoculated into 96-well microplates (FALCON) at a rate of $10^4$ cells per well in an E199-C medium containing 2% of serum.

After 24 h this medium is replaced, for 48 h of incubation, with the same medium without serum and containing 25 µM sodium ascorbate (incubation medium), with or without the test products. The products, solubilized in DMSO, are added to the culture medium at different concentrations.

a.2) Assay of collagen I:

The amount of collagen I secreted into the medium after 48 h of incubation with or without the products was determined by means of an ELISA (Enzyme-Linked Immuno Sorbent Assay) test.

The incubation medium is collected and transferred to the wells of a microtiter plate (Nunc Immunoplate) containing protease inhibitors. Incubation for 24 h at 4° C. allows the collagen to adhere to the plastic. The plates are then rinsed with PBS (Phosphate Buffered Saline).

After 24 h of incubation at 4° C. with serum albumin to prevent non-specific antibody-plastic binding, anti-human collagen I rabbit antibodies (Institut Pasteur, Lyon, France) are added over 1.5 h at 22° C. After rinsing with PBS, the bound antibodies are disclosed with anti-rabbit IgG goat antibodies (INTERCHIM, Montlugon, France) conjugated with an alkaline phosphatase, which, in the presence of paranitrophenyl phosphate, will produce a paranitrophenol absorbing at 405 nm.

The optical densities obtained are converted to nanograms of collagen using a calibration curve established under the same experimental conditions with purified human collagen I (Institut Jacques Boy, France).

a.3) Statistical interpretation:

The amounts of collagen (mean±standard deviation) secreted by the treated and untreated cells are compared by means of a Student t test. The significance level is taken as 0.05.

In parallel, the viability is checked by means of an MTT test.

a.4) Cell viability test:

At the end of the incubation period, the medium is withdrawn and an MTT test is performed. The cells are incubated for 3 h at 37° C. with 100 µl of a solution containing 0.5 mg/ml of a tetrazolium salt in E199-C medium without phenol red. 100 µl of isopropanol are then added to each well in order to solubilize the blue formazan derivative formed by the mitochondrial succinate dehydrogenases of the living cells. The optical density of this solubilized derivative formed is measured at 540 nm.

b) Results obtained b.1) The protocol described above is applied in order to study the effect of the concentration of ginsenoside $R_0$ on the stimulation of collagen I synthesis.

Table 1 gives the results obtained with compositions respectively containing 0, 1, 2.5 and 10 µg of ginsenoside $R_0$ per ml.

TABLE 1

| Concentration of ginsenoside $R_0$ (µg/ml) | Viability | ng collagen I/ $10^4$ cells/48 h | Stimulation of synthesis |
|---|---|---|---|
| 0 | 100 | 2004 ± 132 | |
| 1 | 95 | 2172 ± 88 | +8% S |
| 2.5 | 100 | 2599 ± 163 | +29% S |
| 10 | 103 | 2889 ± 74 | +44% S |

Table 1 clearly shows the stimulation of collagen I synthesis (S: significant at the 0.05 level).

b.2) Comparable results were obtained starting from the extracts obtained according to Example 1 and Example 2 respectively, and with ginsenoside $R_0$.

These results are collated in Table 2 below.

TABLE 2

| Product | Conc. µg/ml | ng coll. I/ 10,000 HF/ 48 h | % stimulation/ control | p |
|---|---|---|---|---|
| Control Asc. 25 µM + DMSO 0.1% | | 2466 ± 289 | | |
| Example 1 | 1 | 2805 ± 197 | +14% | S (p = 0.021) |
| | 2.5 | 2888 ± 405 | +17% | S (p = 0.045) |
| | 10 | 3501 ± 307 | +42% | S (p = 0.003) |
| Example 2 | 1 | 3026 ± 412 | +23% | S (p = 0.0006) |
| | 2.5 | 3171 ± 385 | +28% | S (p = 0.0008) |
| | 10 | 3544 ± 310 | +44% | S (p = 0.0006) |
| Ginsenoside $R_0$ | 1 | 2482 ± 276 | +1% | NS |
| | 1.5 | 3529 ± 516 | +43% | S (p = 0.024) |
| | 10 | 4099 ± 480 | +66% | S (p = 0.002) |

EXAMPLE 4

Demonstration of stimulation of collagen III synthesis a) Protocol:

The protocol is the same as that described with collagen I except that the ELISA is directed against collagen III (human) and the culture treatment time is 72 h instead of the 48 h with collagen I.

b) Results:

In the presence of $R_0$, the synthesis of collagen III is stimulated:

at 2.5 µg/ml: +33% 10 µg/ml: +81%.

Various Examples of cosmetic or pharmaceutical compositions, especially dermatological compositions, are given below, again without implying a limitation.

EXAMPLE 5

Cosmetic composition promoting the formation of the skin tissue system

| Ginsenoside $R_0$ | 0.3 g |
|---|---|
| Ethanol | 2.0 g |
| Preservative | 0.2 g |
| 1.25% Carbopol 940 ® gel . . . qsp | 100 g |

Application: twice a day to the areas of the body requiring prevention or treatment against the effect of "loosening" of the skin.

EXAMPLE 6

Cosmetic composition for firming the skin

| Ginsenoside $R_0$ | 0.6 g |
|---|---|
| Hyaluronic acid | 0.1 g |
| Centella asiatica extract | 0.4 g |
| Excipient + preservative . . . qsp | 100 g |

Application: by local massage twice a day to the areas to be treated, for 4 weeks.

EXAMPLE 7

Ointment for healing skin wounds

| Ginsenoside $R_0$ | 1 g |
|---|---|
| Vitamin A palmitate | 0.05 g |
| Zinc oxide | 0.1 g |
| Glycerol | 1 g |
| Excipient for ointment . . . qsp | 100 g |

EXAMPLE 8

Healing powder

A powder composed of complex solid particles is prepared by following the process described in French patent FR 2 695 635. This powder has the following composition by weight:

nylon powder (carrier particle consisting of particles with a mean diameter of about 20 µm): 97 ecdysterone: 1 ginsenoside $R_0$: 2.

This powder is applied locally to lesions of the ulcer type, 2 to 3 times a day, after antiseptic cleansing of the lesions.

EXAMPLE 9

Culture medium promoting the production of collagen by fibroblasts

The medium comprises:

| Ginsenoside $R_0$ | 10 mg |
|---|---|
| Retinoic acid | 0.3 mg |
| Ascorbic acid | 1.8 mg |
| Proline | 25 mg |
| Glycine | 20 mg |
| Lysine | 20 mg |
| E199-C medium . . . qsp | 100 ml |

What is claimed is:

1. A method of treatment of a mammal comprising administering to said mammal an amount effective to stimulate the synthesis of collagen, of ginsenoside of formula:

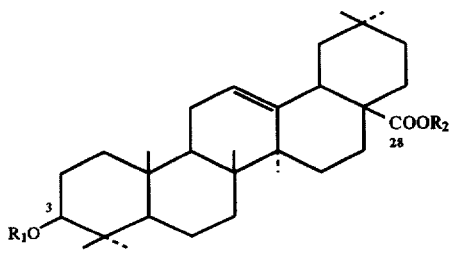

wherein:

the substituent $R_1$ in the 3-position consists of the sugar residues beta-D-glucuronopyranoside and beta-D-glucopyranosyl linked together, represented by GlcA 2Glc, and the substituent $R_2$ in the 28-position is a beta-D-glucopyranosyl residue, represented by Glc; or a plant extract containing it.

2. The method of claim 1, wherein said amount is effective to stimulate the synthesis of collagen selected from the group consisting of collagen I, collagen III and a combination of both.

3. The method of claim 1, wherein said treatment is for treating the effects of skin aging.

4. The method of claim 1, wherein said treatment is for promoting the synthesis of the skin tissue system.

5. The method of claim 1, wherein the treatment is for firming the skin.

6. The method of claim 1, wherein said treatment is for promoting healing or treating collagen deficiencies of the skin.

7. The method of claim 1, wherein the treatment is for healing wounds.

8. The method of claim 1, wherein said ginsenoside is present in a composition in an amount of between 0.001 and 5% by weight based on the total weight of the composition.

9. The method of claim 8, wherein aid composition contains an active substance selected form the group consisting of: *Centella asiatica* extract, asiatic acid, madecassic acid, asiaticoside, a horse chestnut extract, a knee holly extract, madecassoside, ivy saponins, sericoside, alpha-hydroxy acids, alpha-ketoglutarate, ascorbic acid, proline, L-hydroxyproline, lysine, hydroxylysine, glycine, forskolin, a forskolin derivative and a plant extract containing forskolin.

10. The method of claim 1, wherein said ginsenoside is in combination with a collagenase inhibitor.

11. The method of claim 10, wherein said collagenase inhibitor is retinoic acid.

12. A method of performing fibroblast culture comprising introducing into a fibroblast culture medium an amount effective to stimulate the synthesis of collagen by fibroblast cells present in said culture medium, of ginsenoside of formula:

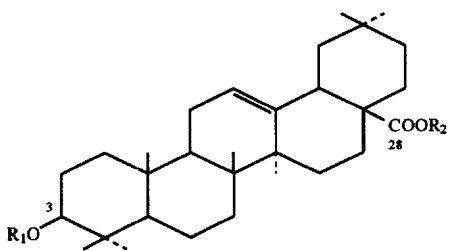

wherein:

the substituent $R_1$ in the 3-position consists of the sugar residues beta-D-glucuronopyranoside and beta-D-glucopyranosyl linked together, represented by GlcA $_2$Glc, and the substituent $R_2$ in the 28-position is a beta-D-glucopyranosyl residue, represented by Glc; or a plant extract containing it.

13. The method of claim 12, wherein said ginsenoside is introduced at a concentration of 0.001 to 0.1% by weight into said culture medium.

14. The method of claim 13, wherein said fibroblast culture medium is an E199 culture medium to which has been introduced L-glutamine at a concentration of 2 mmol/l.

* * * * *